US007835922B2

(12) United States Patent
Sakai et al.

(10) Patent No.: US 7,835,922 B2
(45) Date of Patent: Nov. 16, 2010

(54) DIAGNOSTIC SYSTEM AND METHOD

(75) Inventors: Fumihiko Sakai, Yamato (JP); Minoru Hosoda, Sagamiouno (JP); Itsurou Kobayashi, Sagamiouno (JP); Shinji Kutukake, Sagaminara (JP); Hareaki Yamamoto, Yokohama (JP); Yoneyuki Kobayashi, Yamato (JP); Kouhei Yamashita, Yokohama (JP); Hajime Baba, Osaka (JP); Masahiro Kitamura, Osaka (JP); Toshiyuki Shimizu, Osaka (JP); Yasuzumi Shimizu, Osaka (JP)

(73) Assignee: AstraZeneca AB, Sodertalje (SE), part interest ( * ) Notice: Subject to any disclaimer, the term of this patent is extended or adjusted under 35 U.S.C. 154(b) by 1235 days.

(21) Appl. No.: 11/170,910

(22) Filed: Jun. 29, 2005

(65) Prior Publication Data

US 2006/0009683 A1 Jan. 12, 2006

Related U.S. Application Data

(60) Provisional application No. 60/586,158, filed on Jul. 8, 2004.

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .............................................. 705/2; 705/3
(58) Field of Classification Search .................. 705/2–3
See application file for complete search history.

(56) References Cited

U.S. PATENT DOCUMENTS

| 1,165,465 | A | * | 12/1915 | Taylor | .......................... 434/427 |
| 1,892,318 | A | * | 12/1932 | Pressey | ....................... 434/354 |
| 3,370,789 | A | | 2/1968 | Sherman | |
| 4,130,881 | A | | 12/1978 | Haessler et al. | |
| 4,196,529 | A | * | 4/1980 | Esbensen | ..................... 434/327 |

(Continued)

FOREIGN PATENT DOCUMENTS

WO      02/09004      1/2002

OTHER PUBLICATIONS

Cady "Diagnosis of Headache," *Treating the Headache Patient* (1995) pp. 101-122.

(Continued)

*Primary Examiner*—Robert W Morgan
*Assistant Examiner*—Joy Chng
(74) *Attorney, Agent, or Firm*—Pepper Hamilton LLP (57) ABSTRACT

A diagnostic system and method. In one embodiment, the invention is a diagnostic system comprising: a form comprising one or more diagnostic questions and one or more possible answers to each diagnostic question; a first overlay comprising one or more windows and one or more diagnostic fields, wherein when the first overlay is positioned over the form, the answers to the diagnostic questions that are indicative of the user having a first medical condition are visible through the windows of the first overlay; and wherein the one or more diagnostic fields contain criteria for diagnosing the user with the first medical condition based on the user's selection of answers on the form that are visible through the windows of the first overlay. In other embodiments, the invention is a computer-based version of the diagnostic system and a diagnostic method.

25 Claims, 10 Drawing Sheets

U.S. PATENT DOCUMENTS

| | | | |
|---|---|---|---|
| 4,543,957 A | 10/1985 | Friedman et al. | |
| 4,627,818 A | 12/1986 | Von Fellenberg et al. | |
| 5,379,214 A | 1/1995 | Arbuckle et al. | |
| 5,471,382 A | 11/1995 | Tallman et al. | |
| 5,660,176 A | 8/1997 | Iliff | |
| 5,673,691 A | 10/1997 | Abrams et al. | |
| 5,711,297 A | 1/1998 | Iliff | |
| 5,722,418 A | 3/1998 | Bro | |
| 5,724,968 A | 3/1998 | Iliff | |
| 5,727,949 A * | 3/1998 | Bar-Or et al. | 434/267 |
| 5,741,211 A | 4/1998 | Renirie et al. | |
| 5,868,669 A | 2/1999 | Iliff | |
| 5,910,107 A | 6/1999 | Iliff | |
| 5,913,686 A | 6/1999 | VanWinkle | |
| 5,964,700 A | 10/1999 | Tallman et al. | |
| 5,993,386 A | 11/1999 | Ericsson | |
| 5,995,868 A | 11/1999 | Dorfmeister et al. | |
| 6,022,315 A | 2/2000 | ILiff | |
| 6,071,236 A | 6/2000 | Iliff | |
| 6,108,635 A | 8/2000 | Herren et al. | |
| 6,133,540 A | 10/2000 | Weiss et al. | |
| 6,177,940 B1 | 1/2001 | Bond et al. | |
| 6,206,829 B1 | 3/2001 | Iliff | |
| 6,269,339 B1 | 7/2001 | Silver | |
| 6,284,794 B1 * | 9/2001 | Olesen et al. | 514/565 |
| 6,292,688 B1 | 9/2001 | Patton | |
| 6,334,192 B1 | 12/2001 | Karpf | |
| 6,339,410 B1 | 1/2002 | Milner et al. | |
| 6,416,480 B1 | 7/2002 | Nenov | |
| 6,436,036 B1 | 8/2002 | Miller-Kovach et al. | |
| 6,468,210 B1 | 10/2002 | Iliff | |
| 6,475,143 B2 | 11/2002 | Iliff | |
| 6,482,156 B2 * | 11/2002 | Iliff | 600/300 |
| 6,503,085 B1 | 1/2003 | Elkind | |
| 6,524,241 B2 | 2/2003 | Iliff | |
| 6,527,713 B2 | 3/2003 | Iliff | |
| 6,537,213 B2 | 3/2003 | Dodds | |
| 6,549,804 B1 | 4/2003 | Osorio et al. | |
| 6,569,093 B2 | 5/2003 | Iliff | |
| 6,572,542 B1 | 6/2003 | Houben et al. | |
| 6,607,483 B1 | 8/2003 | Holland | |
| 6,652,457 B1 | 11/2003 | Skiba et al. | |
| 6,663,564 B2 | 12/2003 | Miller-Kovach et al. | |
| 6,725,209 B1 | 4/2004 | Iliff | |
| 6,730,027 B2 | 5/2004 | Iliff | |
| 6,746,399 B2 | 6/2004 | Iliff | |
| 6,764,447 B2 | 7/2004 | Iliff | |
| 6,767,325 B2 | 7/2004 | Iliff | |
| 6,817,980 B2 | 11/2004 | Iliff | |
| 6,849,045 B2 | 2/2005 | Iliff | |
| 6,878,885 B2 | 4/2005 | Miller-Kovach et al. | |
| 6,957,038 B1 * | 10/2005 | Gartner et al. | 434/354 |

OTHER PUBLICATIONS

Cockcroft "An intermediate-technology pattern matching model of veterinary diagnosis," *Tropical Animal Health and Production*, (1999) 31(3):127-134.

Nash et al., "Differential diagnosis, an apparatus to assist the logical faculties," *Lancet* (1954) 266(6817):874-875.

Werneke et al., "A descriptive study of the centralization phenomenon. A prospective analysis," *Spine* (1999) 24(7):676-683.

* cited by examiner

FIG. 1

IF YOU SUFFER FROM HEADACHE, PLEASE VISIT AND CONSULT WITH US
WE ARE ACTIVELY ENGAGED IN TREATMENT OF HEADACHE.

**MIGRAIN-QUEST:
QUESTIONNAIRE ON HEADACHE**

PLEASE NOTE THAT HEADACHE CAUSED BY THE FOLLOWING
ARE EXCLUDED FROM THIS QUESTIONNAIRE;
● COLD ● HANGOVER ● OTITIS MEDIA ● DENTAL CARIES ● HEAD INJURY

PLEASE ANSWER THE QUESTIONS BELOW.

Q1. DID YOU EXPERIENCE HEADACHE IN THE LAST SEVERAL YEARS? (CHOOSE ONE ANSWER ONLY)
1. YES → (GO TO Q3)
2. NO → (THIS IS THE END OF THE QUESTIONNAIRE. THANK YOU FOR YOUR COOPERATION.)

Q2. DID YOU THINK OF BEING ABSENT FROM OR DID YOU EXPERIENCE DIFFICULTY IN DOING YOUR DAILY WORK SUCH AS JOB, SCHOOL, HOUSEHOLD WORK AND PERSONAL OCCASION WHICH WAS UNABLE TO CARRY ON AS USUAL DUE TO HEADACHE?
1. YES → (GO TO Q3)
2. NO → (THIS IS THE END OF THE QUESTIONNAIRE. THANK YOU FOR YOUR COOPERATION.)

IF YOU CIRCLE YES IN THE Q2, PLEASE GO TO Q.3.

FIG. 2A

Q3. HOW OFTEN DID YOU HAVE HEADACHE? (MARK ALL THAT APPLY)
1. SOMETIMES    2. ALMOST EVERY DAY

Q4. HOW LONG DID YOUR HEADACHE LAST IF YOU DIDN'T TAKE MEDICINE SUCH AS A PAINKILLER? (MARK ALL THAT APPLY)
1. LESS THAN 30 MIN   2. 30MIN-3HOURS   3. 4 HOURS-3 DAYS
4. 4-7 DAYS   5. MORE THAN 7 DAYS - EVERY DAY

Q5. DID YOU HAVE THE EXPERIENCE OF SCINTILLATING SCOTOMATA AND VISUAL DEFECT AS AURA?
1. YES    2. NO

Q6. WHERE WAS THE LOCATION OF THE PAIN? (MARK ALL THAT APPLY)
1. UNILATERAL    2. OCCIPITAL REGION, NECK AND TEMPLE    3. BILATERAL

Q7. HOW WAS THE FEELING OF THE PAIN? (MARK ALL THAT APPLY)
1. PULSATING, POUNDING OR THROBBING
2. PRESSURE/BAND-LIKE TIGHTENING QUALITY
3. PAIN ASSOCIATED WITH STIFFNESS AROUND SHOULDER AND HEAD
4. PAIN PERSISTS SLUGGISHLY

Q8. HOW WAS THE SEVERITY OF THE PAIN? (MARK ALL THAT APPLY)
1. PREFER TO AVOID ACTIVITY AND TO SLEEP WHEN SEVERE
2. PREFER TO LIE STILL
3. TOLERABLE (JOB OR HOUSEHOLD ETC CAN BE MANAGED TO DO)

Q9. HAS YOUR HEADACHE EVER BEEN SO BAD, WHEN YOU HAD DONE BELOW THINGS? (MARK ALL THAT APPLY)
1. TAKE A BATH
2. MOVE THE BODY (PHYSICAL ACTIVITY SUCH AS RUNNING BY WALKING STAIRS)
3. NOT SO BAD

Q10. DID YOU EXPERIENCE THE FOLLOWING WHEN YOU HAD HEADACHE? (MARK ALL THAT APPLY)
1. NAUSEA
2. VOMITING
3. INCREASED SENSITIVITY TO NOISE (FEEL NOISE MORE IRRITATING OR AS IF PIERCING YOUR HEAD)
4. INCREASED SENSITIVITY TO LIGHT (FEEL LIGHT MORE IRRITATING OR GLARING)

DIAGNOSTIC SYSTEM AND METHOD

CROSS-REFERENCE TO RELATED APPLICATION

The present application claims the benefit of United State Provisional Application 60/586,158, filed Jul. 8, 2004, the entirety of which is incorporated herein by reference.

FIELD OF INVENTION

The present invention relates generally to the field of diagnosing a medical condition of a person, and specifically to the field of diagnosing a medical condition of a person based on the person's answers to a set of questions. The invention is particularly suited for the diagnosis of headache based conditions but is not so limited.

BACKGROUND OF INVENTION

Various methods and systems exist for diagnosing medical conditions. However, many of these diagnostic systems and methods require that the subject person meet with a doctor or other health care professional to either carry out the diagnostic method or interpret the data obtained from the diagnostic system or method. Such diagnostic systems and methods are unsatisfactory because many people dislike meeting and/or consulting with doctors or other health care professionals for diagnosis. This results in many people receiving inadequate or no treatment, thereby resulting in a worsening of the medical condition and/or additional harm to the person. For obvious reasons, this is undesirable.

Additionally, many existing diagnostic methods and systems are either very complicated to use or are expensive. Thus, these diagnostic systems and methods result in a large percentage of the population going untreated. Still, other diagnostic systems and methods are unreliable.

While diagnostic systems and methods that are purely computer based have become more popular, computer based diagnostic systems require that the user both have a computer and be aware of the diagnostic software. A further drawback of such computer based systems is that they tend to be expensive and require a working knowledge of the software and its functionality.

One particular area that has seen an increase in either misdiagnosis or failure of patients to seek diagnosis is that of headaches. Migraine, tension-type headaches, and other types of headache-based medical conditions often go undiagnosed because most primary care physicians do not have the expertise in diagnosing these conditions. Additionally, many people do not want to seek professional attention for a medical condition for which they are uncertain of having.

SUMMARY OF THE INVENTION

It is therefore an object of the present invention to provide a new diagnostic system and method.

Another object of the present invention is to provide a diagnostic system and method that can be used by people for self-diagnosis in the comfort of their own homes.

Yet another object of the present invention is to provide a diagnostic system and method that gives a user an indication that there is an increased likelihood of having a medical condition.

Still another object of the present invention is to provide a diagnostic system and method that motivates people to seek additional profession help for a medical condition.

A further object of the present invention is to provide a diagnostic system and method that is easy to use, understand, and/or distribute.

A yet further object of the present invention is to provide a diagnostic system and method that is cost-effective to manufacture.

A still further object of the present invention is to provide a system and method for diagnosing headache related medical conditions.

These and other object are met by the present invention which, in one embodiment, is a diagnostic system comprising: a form comprising one or more diagnostic questions and one or more possible answers to each question; a first overlay comprising one or more windows and one or more diagnostic fields, wherein when the first overlay is positioned over the form, answers indicative of the user having a first medical condition are visible through the windows of the first overlay; and wherein the one or more diagnostic fields contain criteria for diagnosing the user with the first medical condition based on the user's selection of answers that are visible through the windows of the first overlay.

In another embodiment, the invention is a diagnostic method comprising: a) answering one or more diagnostic questions pertaining to a user's health by selecting one or more answers, the one or more diagnostic questions and answers being provided on a form; b) positioning a first overlay having one or more windows and one or more diagnostic fields atop the form so that the answers indicative of the user having a first medical condition are visible through the windows of the first overlay; and c) using criteria in the diagnostic fields of the first overlay, diagnosing the user with the first medical condition based on the user's selection of answers that are visible through the windows of the first overlay.

In still another embodiment, the invention is a computer-based diagnostic system comprising: means for displaying an electronic form having one or more diagnostic questions and corresponding answers to the diagnostic question, each set of answers containing at least one answer that is indicative of the user having a first medical condition; means for a user to select one or more of the answers; means for identifying the answers selected by the user that are indicative of the user having the first medical condition; and means for diagnosing the user with the first medical condition based on the user's selection of answers that are indicative of the user having the first medical condition.

BRIEF DESCRIPTION OF THE DRAWINGS

FIG. 2B is a back view of the questionnaire form of the headache diagnostic system of FIG. 1.

DETAILED DESCRIPTION OF THE DRAWINGS

Figure 1:
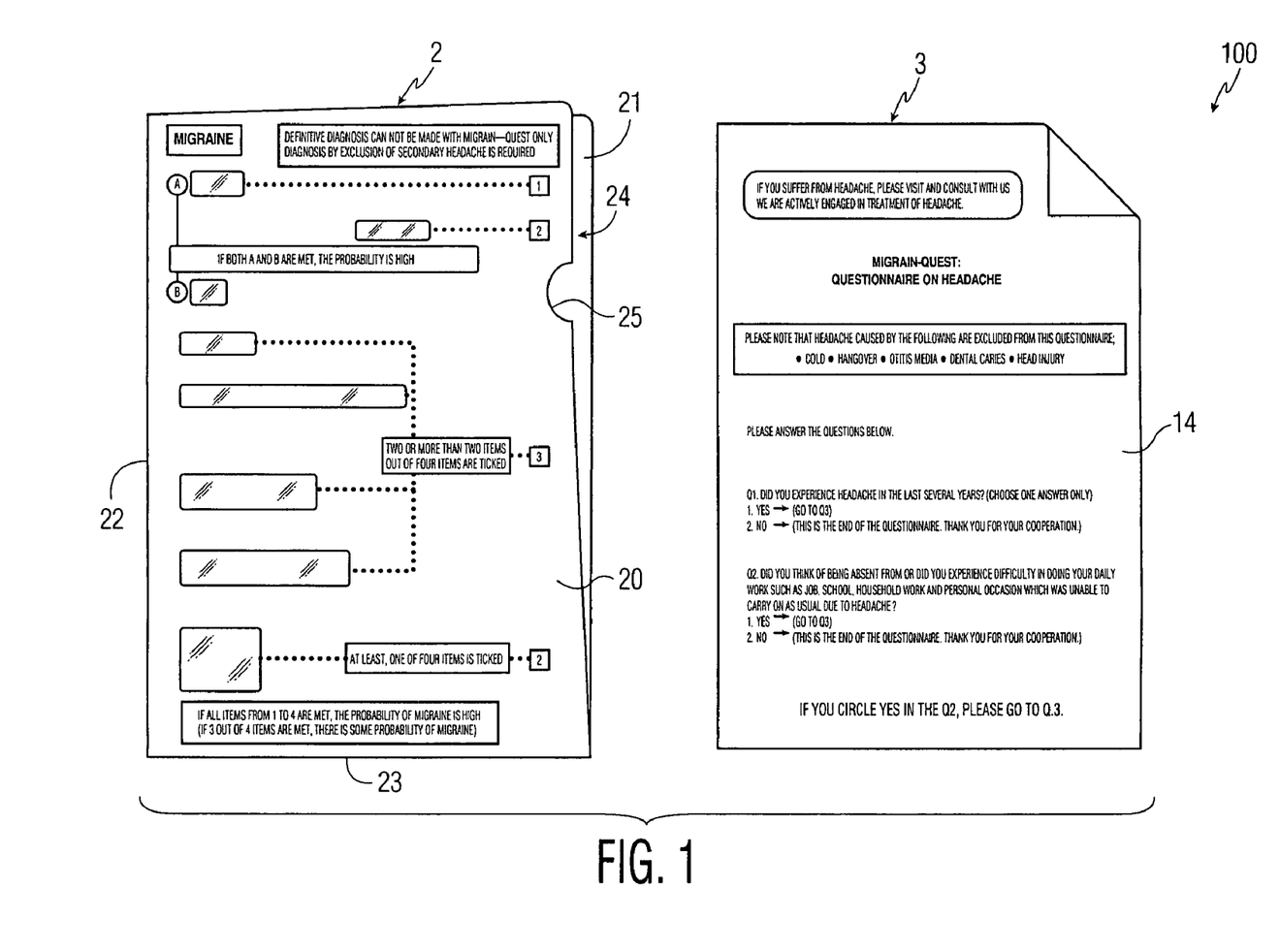
FIG. 1 is a front perspective view of a headache diagnostic system according one embodiment of the invention.

FIG. 1 illustrates a headache diagnostic system 100 according to an embodiment of the present invention. The headache diagnostic system 100 comprises a diagnostic file 2 and a questionnaire sheet/form 3. While the illustrated embodiment of the diagnostic system 100 is specifically designed for the diagnosis of headaches, such as migraines and tension-type headaches, the invention is not so limited. Those skilled in the art will understand that the invention can be adapted for diagnosis of almost any type of medical condition (mental or physical), health status, or physiological impairment. As used herein, the term diagnosis, and all derivative thereof, is intended to encompass definitive diagnosis of medical conditions along with determinations of increased or decreased likelihood of having or not having a medical condition so that the user can seek a definitive diagnosis from a healthcare professional.

The diagnostic file 2 comprises a first overlay 20 and a second overlay 21. The first and second overlays 20, 21 are formed from a single piece of material that is folded in half at crease 22. Once creased, the first and second overlays 20, 21 are connected to one another along the bottom edge 23. As a result, the first and second overlays 20, 21 are connected along two sides, thereby forming a pocket 24 capable of slidably receiving questionnaire form 3 from either of the two open sides. The connection along bottom edge 23 can be accomplished by a low heat weld or the proper use of sutures, staples, adhesive, tape, a tongue and groove assembly, stamping, or the like. A thumbnail cutout 25 is provided along the side of the first overlay 20 along the open lateral side of the diagnostic file 2 so as to afford easy separation of the first and second overlays 20, 21 during the insertion of the questionnaire form 3. This cutout 25 can take on any desired shape or size.

In other embodiments of the invention, the first and second overlays 20, 21 of the diagnostic file 2 can be separate pieces of material that are connected along one or more edges using one of the above identified connection techniques to form the diagnostic file 2. The overlays 20, 21 can be formed of one or more layers of thin flexible materials, such as plastic, paper, synthetic polymers, or the like. The diagnostic file 2 is preferably sized so that pocket 24 fully receives a standard sized piece of paper, such as A-4 or 8.5×11.5 paper sizes. However, the invention is not limited to any specific material of construction or dimensions. In some embodiments of the invention, only a single overlay 20 or 21 may be used in combination with the questionnaire form 3 to diagnose a medical condition. In such embodiments, the overlay 20 or 21 will be simply positioned over and aligned with the questionnaire form 3 during use.

The questionnaire form 3 is a sheet of paper comprising screening questions on one side and diagnostic questions on the opposite side. The screening questions and the diagnostic questions are carefully selected to diagnose a targeted medical condition (in this case migraines and tension-type headaches) and printed on the questionnaire form 3 prior to distribution in a predetermined pattern. This will be discussed in greater detail below. The questionnaire form 3 can be made of a variety of materials which can be written on or otherwise marked, including without limitation, paper, plastic, cardboard, metal, etc. If desired, the questionnaire form 3 can be constructed to be either disposable or reusable. For example, in a reusable embodiment, the questionnaire form 3 may be formed of plastic (or comprise a plastic or polymer coating) from which pencil, ink, or marker indicia can be easily erased. In disposable embodiments, a simple piece of paper may be used for ease of reproduction and to reduce manufacturing costs.

Figure 2A:
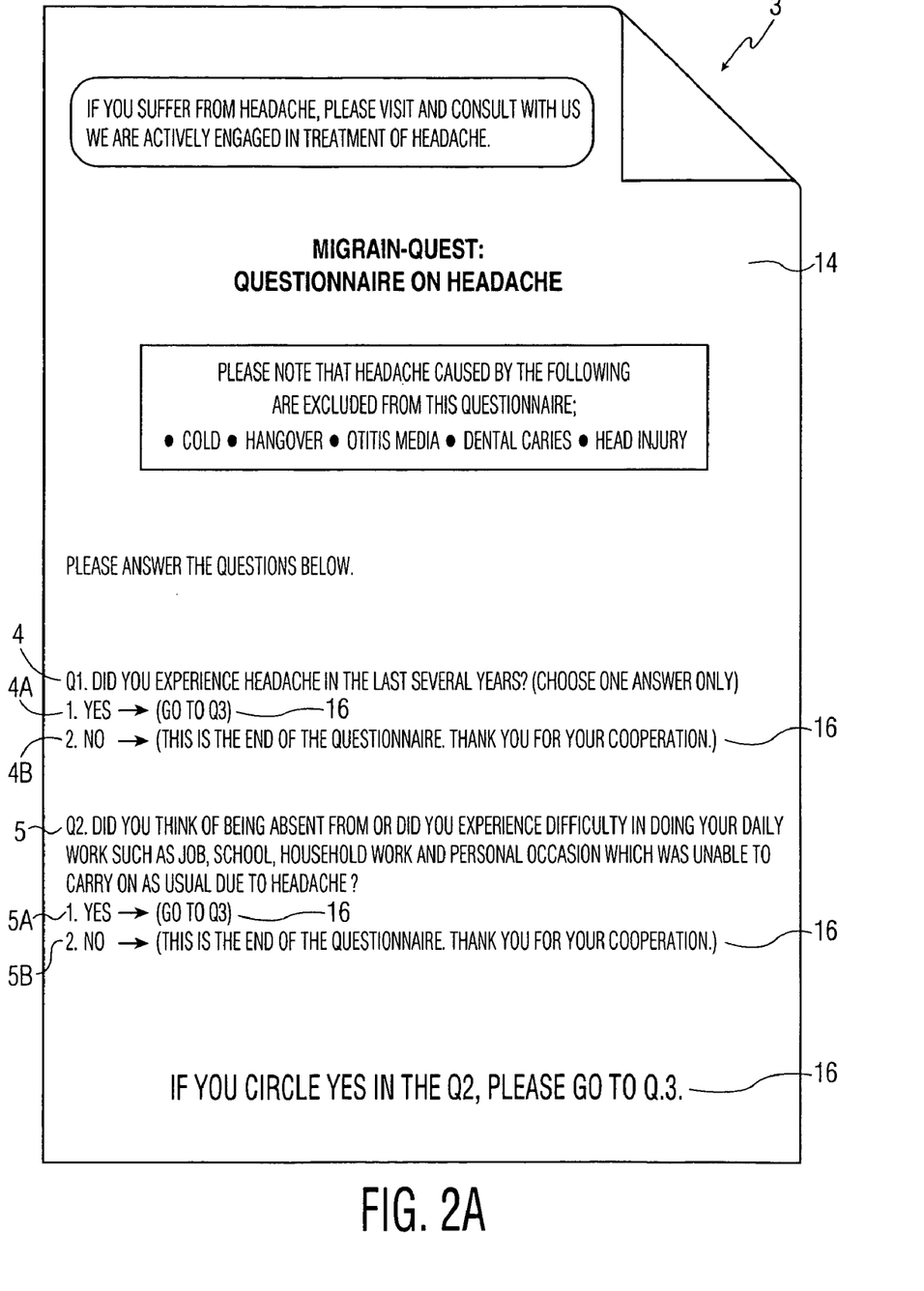
FIG. 2A is a front view of the questionnaire form of the headache diagnostic system of FIG. 1.

Referring now to FIGS. 2A and 2B, the questionnaire form 3 is illustrated according to an embodiment of the present invention. The questionnaire form 3 is a sheet of paper comprising screening questions 4-5 on one side (FIG. 2A) and diagnostic questions 6-13 on the opposite side (FIG. 2B). The questionnaire form 3 is designed with the intention that the user answer the screening questions 4-5 on the first side before proceeding to the second side of the questionnaire form to answer the diagnostic questions 6-13.

Referring solely to FIG. 2A, the first side 14 of the questionnaire form 3 comprises two screening questions 4-5. While two screening questions 4-5 are used in the example, any number of screening questions may be used. The exact number of screening questions will be dictated on a case-by-case basis, considering such factors as the type of medical condition being diagnosed, target patient group, etc. In some embodiments of the questionnaire form 3, the screening questions may be omitted. In such embodiments, the first side 14 of the questionnaire form 3 may be identical to the second side 15 (FIG. 2B), contain different diagnostic questions, or contain general user instructions and/or advertisements.

A choice of corresponding answers 4A-4B and 5A-5B are provided on the first side 14 of the questionnaire form 3 that respectively correspond to the screening questions 4, 5. The first side 14 further comprises instructions 16 for determining whether, based on the user's answers to the screening questions 4-5, the user needs to proceed with answering the next screening question and/or the diagnostic questions 6-13 on the second side 15 of the questionnaire form 3.

In the illustrated embodiment of the questionnaire form 3, which is designed for migraine and/or tension-type headache diagnosis, the screening questions 4-5 respectively pertain to whether the user experienced a headache in the last several years and whether the onset of such headaches affected the user's ability to carry out their daily routine. Regarding screening question 4 specifically, each possible answers 4A, 4B has corresponding instructions 16 which, depending on the answer 4A, 4B selected, will direct the user to either proceed to the next screening question 5 or cease further completion of the questionnaire form 3. Regarding screening question 5 specifically, each possible answers 5A, 5B has corresponding instructions 16 which will direct the user to either proceed to answer the diagnostic questions 6-13 on the second side 15 of the questionnaire form 3 or cease further completion of the questionnaire form 3.

The screening questions 4, 5 are designed so that if the user selects an answer (which in this case are answers 4B or 5B) that correspond to instructions 16 that instruct the user to cease further completion of the questionnaire form 3, the diagnosis is that the user does not have (or at least is not likely to have) the medical condition(s) being screened for, which in this case is migraine and tension-type headaches. However, if the user selects answers (which in this case are both answers 4A or 5A) that correspond to instructions 16 that instruct the user to continue with completion of the second side 15 of the questionnaire form 3, the user has not been screened out, and is likely in need of further diagnosis/inquiry, which in this case is additional diagnosis for migraine and tension-type headaches.

Referring now to FIG. 2B, the second side 15 of the questionnaire form 3 is illustrated. Eight diagnostic questions 6-13 are provided on the second side 15 of the questionnaire form 3. The diagnostic questions 6-13 are carefully drafted and selected so that the user's answers are indicative of the user having or not having a certain medical condition within a reasonable degree of medical certainty, which in this case is migraines and/or tension-type headaches. Specifically, diagnostic question 6 pertains to the frequency of which a user experiences headaches. Diagnostic question 7 pertains to how long the user's headaches last if no medication is taken. Diagnostic question 8 pertains to whether the user experiences the onset of aura symptoms during headaches, such scintillating scotomata and/or visual defect. Diagnostic question 9 pertains to the location of the headache pain. Diagnostic question 10 pertains to the type of headache pain. Diagnostic question 11 pertains to the severity of the user's headache pain. Diagnostic question 12 pertains to whether the user's performance of certain physical activities affects/worsens the headache pain. Diagnostic question 13 pertains to whether the user experiences the onset of additional headache-related symptoms.

While a total of eight diagnostic questions 6-13 are used in the illustrated questionnaire form, the invention is not so limited. Any combination of the diagnostic questions 6-13 can be used and/or other diagnostic questions can be added if desired. However, it is preferable that testing and/or research be performed to determine the proper number, identity, and combination of diagnostic questions that will reliably diagnose the target medical condition(s) within a certain degree of accuracy. It has been determined that the diagnostic questions 6-13 are reliable in diagnosing migraine and/or tension-type headaches.

Each diagnostic question 6-13 has one or more possible answers 6A-13D that correspond to the appropriate diagnostic question 6-13. (Questions and answers having like numerical prefixes correspond to one another.) The answer choices for each diagnostic question 6-13 have one or more answers that are indicative of a person having a targeted medical condition, which in this case is migraines and/or tension-type headaches. For example, answers 6A and 6B correspond to diagnostic question 6. As will be explained in detail below with respect to FIG. 5, answer 6A is indicative of the user having migraines, while answer is 6B is not. Some diagnostic questions 6-13 can have multiple answers that are indicative of the user having a targeted medical condition. In some cases, one answer can be indicative of more than one medical condition being targeted. The positioning and arrangement of the answers 6A-13D on the questionnaire form 3 are chosen so that answers indicative of the user having the medical condition being diagnosed are in a corresponding spatial relationship to the windows 26 of the diagnostic file 2.

Figure 3A:
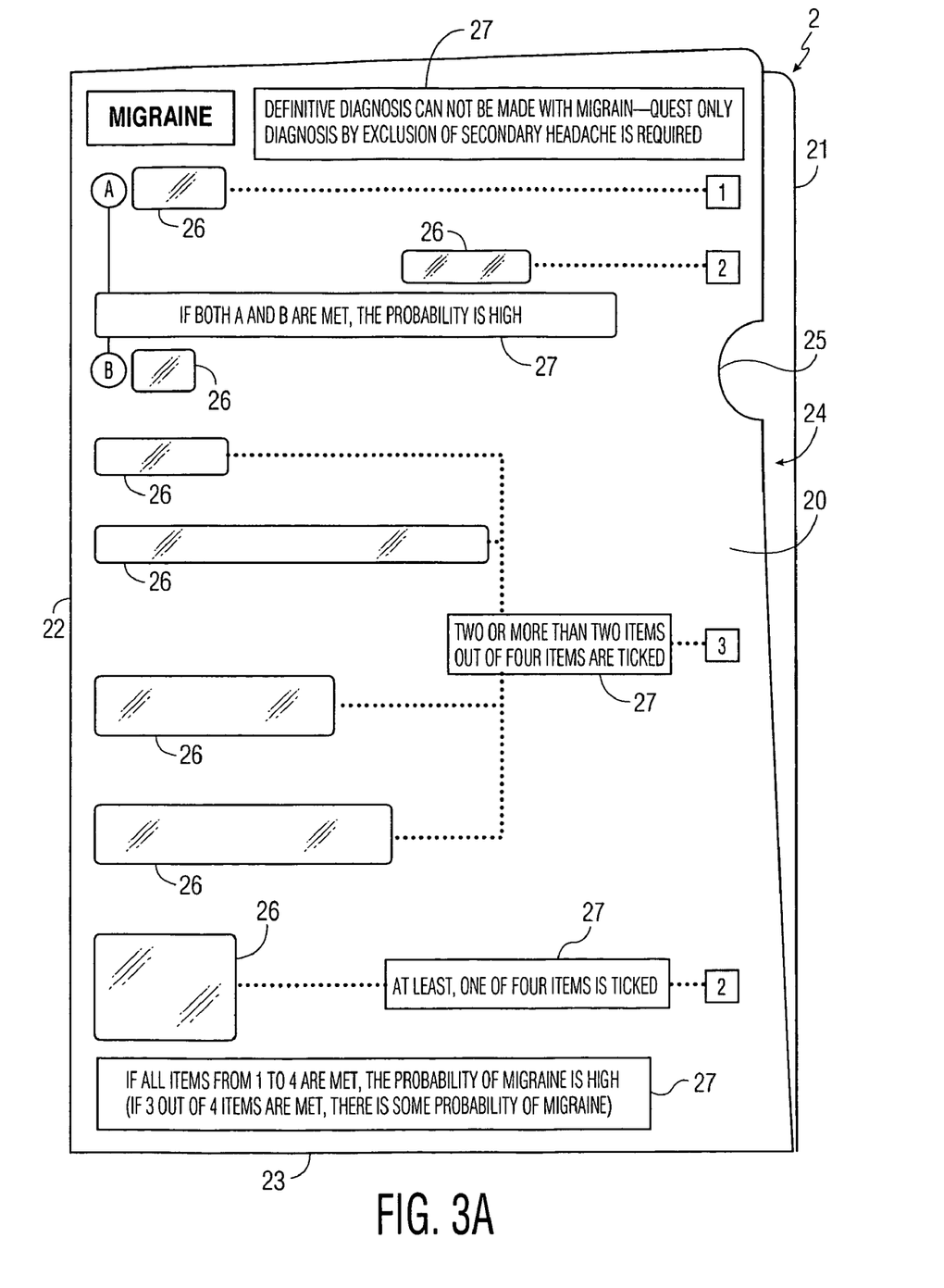
FIG. 3A is a front view of the diagnostic file of the headache diagnostic system of FIG. 1 showing the first overlay in detail.
Figure 3B:
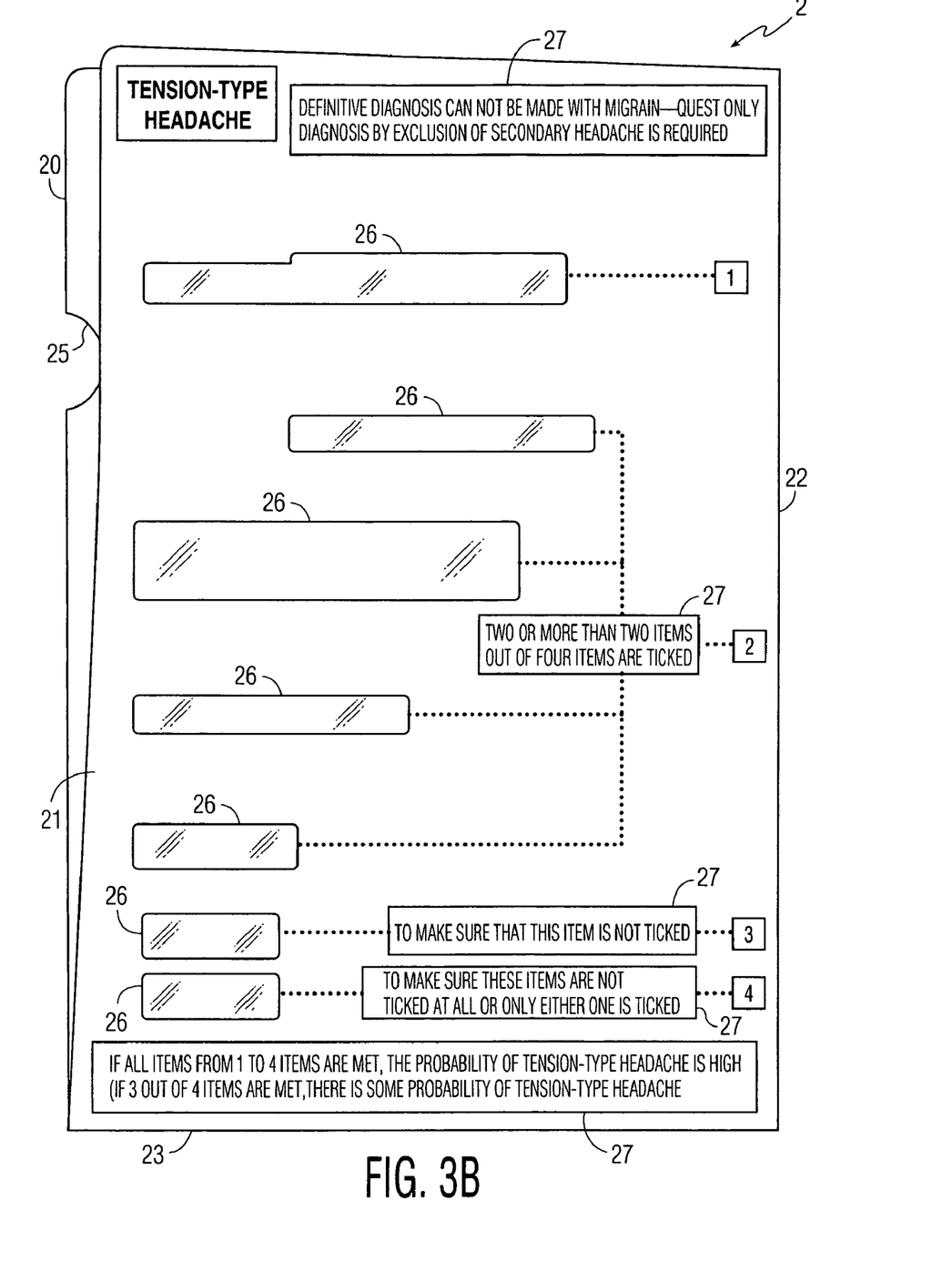
FIG. 3B is a front view of the diagnostic file of the headache diagnostic system of FIG. 1 showing the second overlay in detail.

Referring now to FIGS. 3A and 3B, the first overlay 20 and second overlay 21 of the diagnostic file 2 are illustrated in detail. The construction of the diagnostic file 2 has already been discussed above in relation to FIG. 1.

FIG. 3A. is a front view of the first overlay 20, which is specifically designed for use in combination with the second side 15 of the questionnaire form 3 to diagnose migraines. The first overlay 20 of the diagnostic file 2 comprises a plurality of transparent windows 26 spatially arranged at predetermined locations and designed to be a predetermined size. Each window 26 is designed so that only those answers on the questionnaire form 3 that are indicative of the user having migraines will be visible therethrough when the questionnaire form 3 is fully inserted into the pocket 24 with the second side 15 of the questionnaire form 3 facing the first overlay 20. While the windows 26 are transparent sections of the first overlay 20, the windows 26 can be formed in a variety of ways, including cutouts, etc. In some embodiments, the entire overlay 20 may be constructed of a transparent material and the windows 26 may be formed by boxes or other indicia marked on the overlay.

Figure 5:
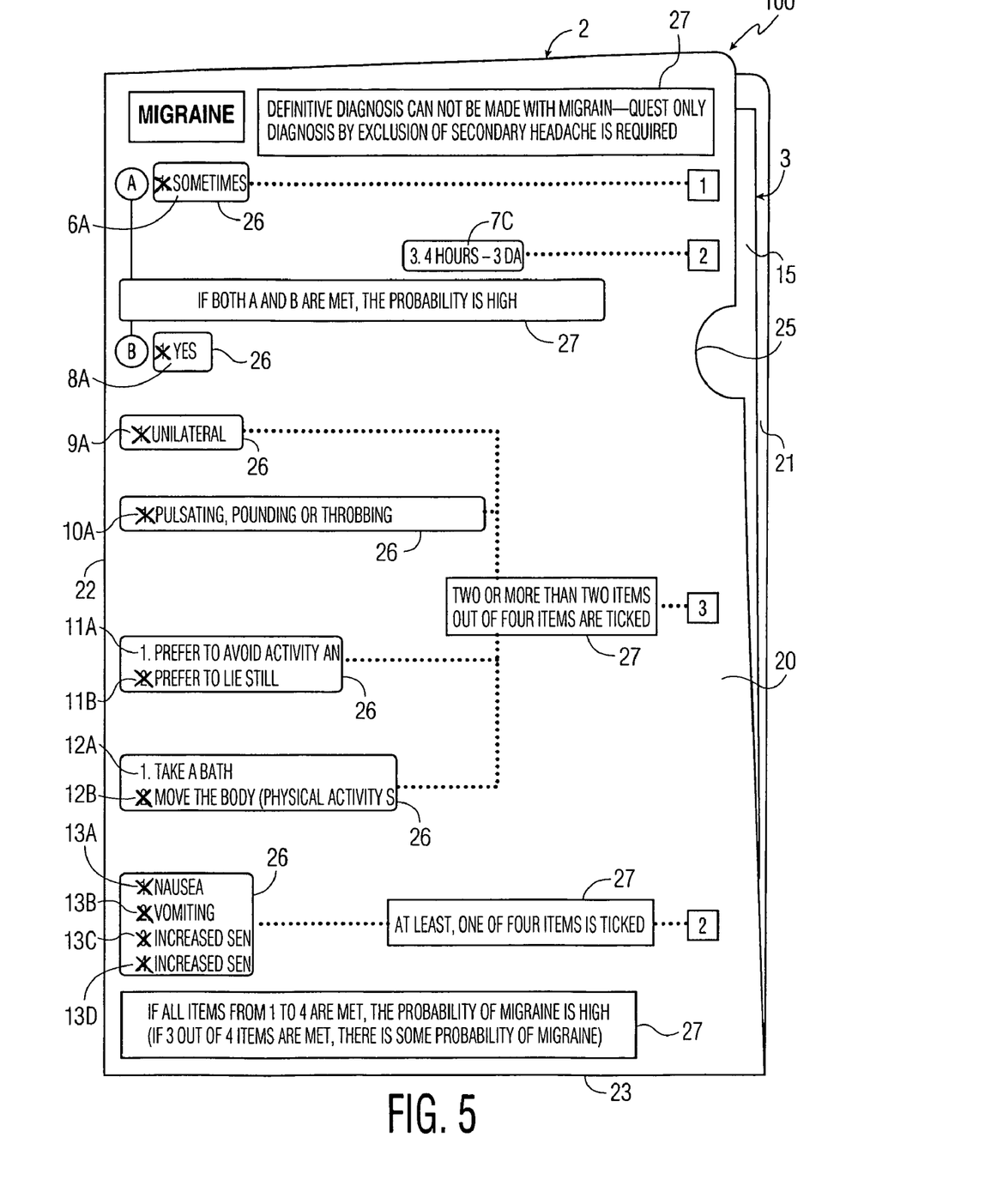
FIG. 5 is a front view of the questionnaire form fully inserted into the diagnostic file for migraine diagnosis using the headache diagnostic system of FIG. 1.

The first overlay 20 further comprises a plurality of diagnostic fields 27. The diagnostic fields 27 contain criteria/instructions for diagnosing the user for migraines based on the user's selection of answers 6A-13D on the questionnaire form 3 that are visible through the windows 26. While the diagnostic fields 27 are illustrated as being in a separated/boxed-off areas of the first overlay 20, the invention is not so limited. In some embodiments, the diagnostic fields 27 may be mere areas on the first overlay 20 containing text without any special delineation or demarcation. Only those answers on the questionnaire form 3 that are indicative of the user having migraines are visible through the windows 26 of the first overlay 20 when the questionnaire form 3 is fully inserted into the diagnostic file 2 (as shown in FIG. 5). The diagnostic fields 27 provide the user and/or health professional with the means to be able to perform a quick and reliable interpretation of the user's answers with respect to migraine diagnosis.

Figure 7:
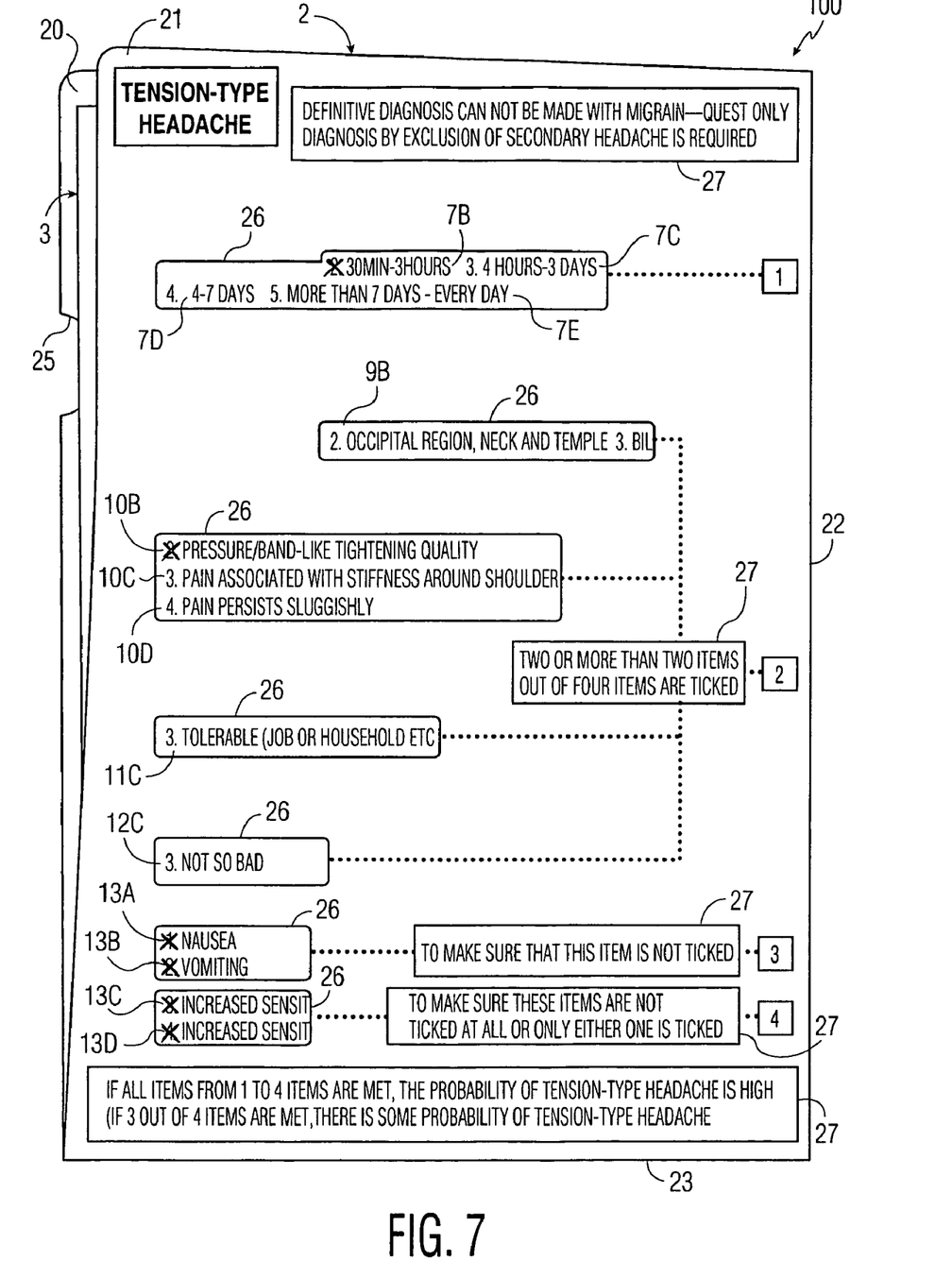
FIG. 7 is a front view of the questionnaire form fully inserted into the diagnostic file for tension-type headache diagnosis using the headache diagnostic system of FIG. 1.

FIG. 3B. is a front view of the second overlay 21, which is specifically designed for use in combination with the second side 15 of the questionnaire form 3 to diagnose tension-type headaches. Similar to that of the first overlay 20, the second overlay comprises a plurality of windows 26 and diagnostic fields 27. However, the positioning and size of each window 26 of the second overlay 21 is designed so that only those answers on questionnaire form 3 that are indicative of the user having tension-type headaches will be visible therethrough when the questionnaire form 3 is fully inserted into the pocket 24 with the second side 15 of the questionnaire form 3 facing the second overlay 21 (as shown in FIG. 7). Additionally, the diagnostic fields 27 of the second overlay 21 contain criteria/instructions for diagnosing the user for tension-type headaches based on the user's selection of answers 6A-13D on the questionnaire form 3 that are visible through the windows 26 of the second overlay 21. Only those answers on the questionnaire form 3 that are indicative of the user having tension-type headaches are visible through the windows 26 of the second overlay 21 when the questionnaire form 3 is fully inserted into the diagnostic file 2 with the second side 15 of the questionnaire form 3 facing the second overlay 21 (as shown in FIG. 7). The diagnostic fields 27 provide the user and/or health professional with the means to be able to perform a quick and reliable interpretation of the user's answers with respect to tension-type headache diagnosis.

Figure 4:
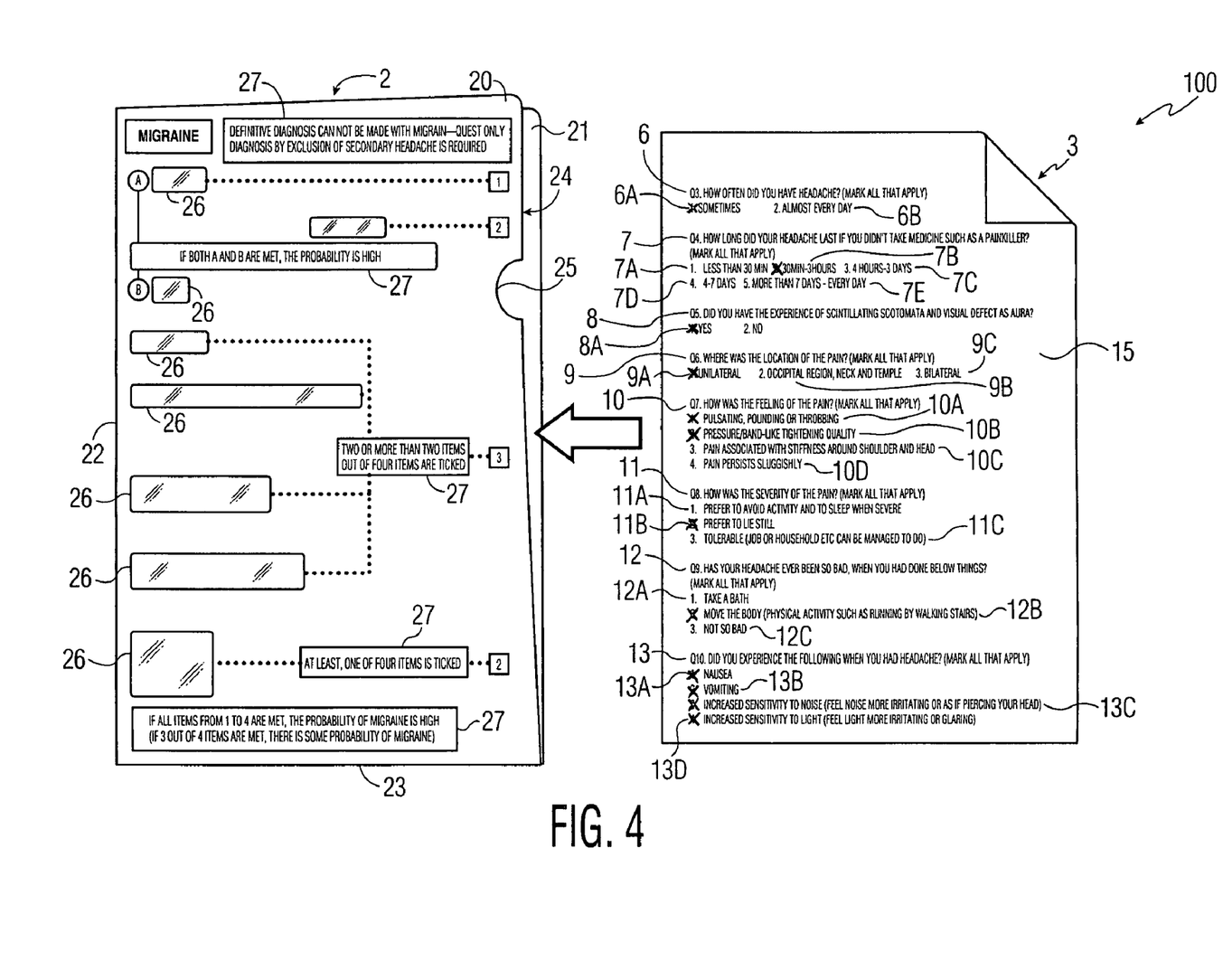
FIG. 4 is a depiction of the questionnaire form being inserted into the diagnostic file for migraine diagnosis using the headache diagnostic system of FIG. 1.

Referring now to FIGS. 4 and 5, the method by which a user is diagnosed with migraines using the headache diagnostic system 100 according to an embodiment of the invention will be discussed. Starting with FIG. 4, the headache diagnostic system 100, which includes the diagnostic file 2 and the questionnaire form 3 is supplied to a user. In some cases, only the questionnaire form 3 will be supplied and a healthcare professional will have the diagnostic file 2. Upon receiving the questionnaire form 3, the user first answers the screening question 4-5 on the first side 14 of the questionnaire form 3 (as discussed above with respect to 2A). Assuming that the user answers the screening questions 4-5 so that he/she is instructed to continue with answering the diagnostic questions 6-13 on the questionnaire form 3, the user then turns to the second side 15 of the questionnaire form 3. The user then reads the diagnostic questions 6-13 and selects the answers 6A-13D that are indicative of the user's health and physical conditions. In the illustration, a hypothetical user has selected his/her answers by marking an "X" on all answer that apply to his/her health status.

Once the user has completed selecting his/her answers 6A-13D to the diagnostic questions 6-13, the user slides/inserts the questionnaire form 3 into the pocket 24 of the diagnostic file 2 between the first and second overlays 20, 21, as indicated by the arrow. The second side 15 of the questionnaire form 3 faces the first overlay 20 at this time. The user continues to insert/slide the questionnaire form 3 into the diagnostic file 2 until the questionnaire form 3 is fully positioned therein (i.e., in a diagnostic position), as shown in FIG. 5.

Referring now to FIG. 5, the components of the headache diagnostic system 100 are arranged for migraine diagnosis, i.e., the questionnaire form 3 is fully and properly inserted into the pocket 24 of the diagnostic file 2 with the first side 14 facing the first overlay 20. As can be seen, only those answers 6A, 7C, 8A, 9A, 10A, 11A, 11B, 12A, 12B, and 13A-13D to the diagnostic questions 6-13 that are indicative of the user having migraines are aligned with and visible through the windows 26 of the first overlay 20. The remaining answers to the diagnostic questions 6-13 are not aligned with the windows 26 and are not visible therethough. Based on the user's selection of answers 6A, 8A, 9A, 10A, 11B, 12B and 13A-D to the diagnostic questions 6-13 that are visible through the windows 26 of the first overlay, and according to the criteria set forth in the diagnostic fields 27 of the first overlay 20, the user can be easily and reliably diagnosed with (or without) migraines. In the hypothetical example, the diagnosis is that there is a very high probability that the user has migraines based on his/her selection of answers 6A, 8A, 9A, 10A, 11B, 12B and 13A-D.

Figure 6:
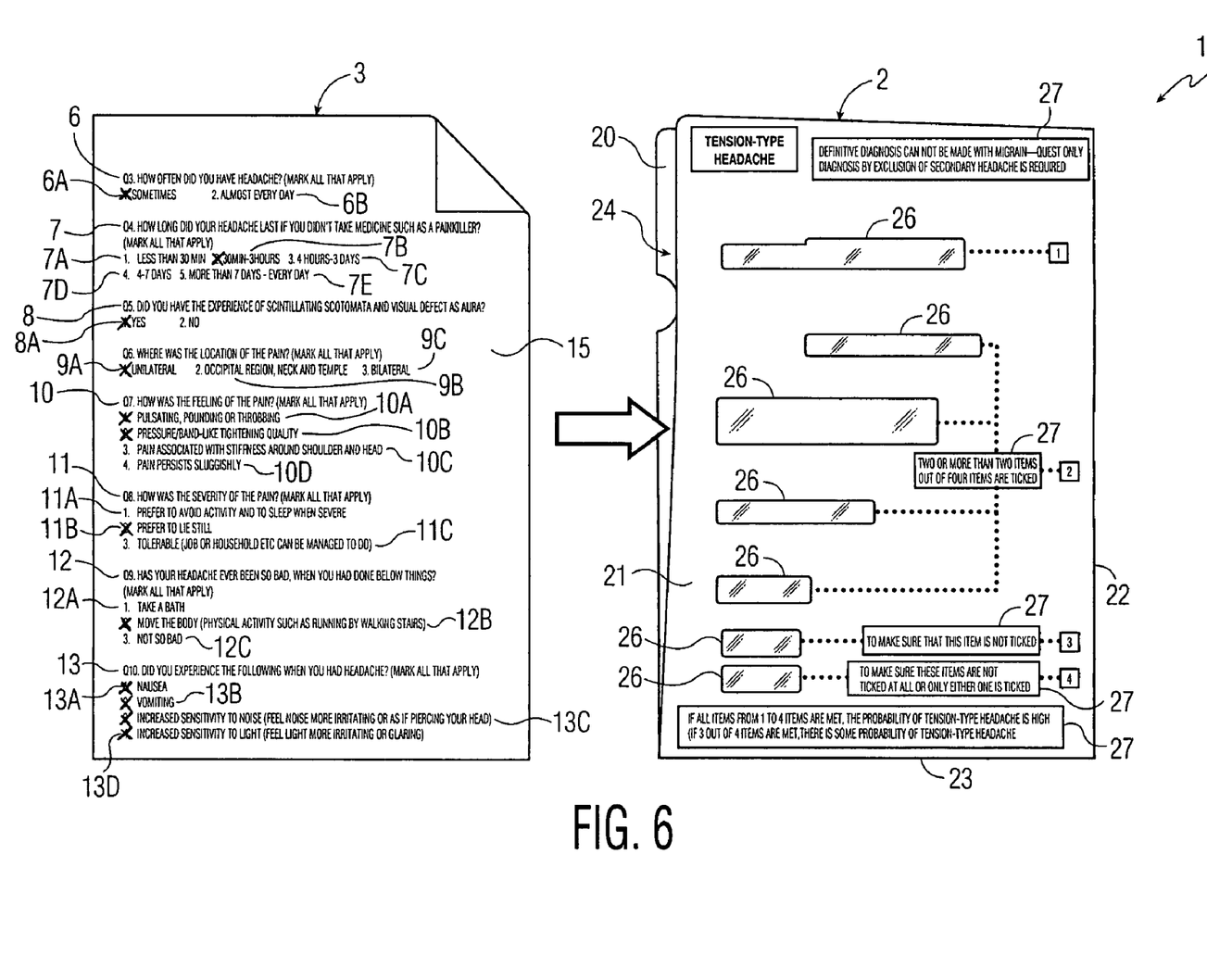
FIG. 6 is a depiction of the questionnaire form being inserted into the diagnostic file for tension-type headache diagnosis using the headache diagnostic system of FIG. 1.

Referring to FIGS. 6 and 7, the headache diagnostic system 100 can also be used to diagnose a user with tension-type headaches in a manner very similar to that described above with respect to migraine diagnosis. The only difference is that after the user has completed answering the diagnostic questions 6-13, the questionnaire form 3 is inserted into the diagnostic file 2 with the second side 15 of the questionnaire form 3 facing the second overlay 21, as shown in FIG. 6.

FIG. 7 illustrates the components of the headache diagnostic system 100 arranged for tension-type headache diagnosis, i.e., the questionnaire form 3 is fully and properly inserted into the pocket 24 of the diagnostic file 2 with the second side 15 facing the second overlay 21. When so positioned, only those answers 7B-7E, 9B, 10B-10D, 11C, 12C, and 13A-13D to the diagnostic questions 6-13 which are indicative of the user having tension-type headaches are aligned with and visible through the windows 26 of the second overlay 21. The remaining answers to the diagnostic questions 6-13 are not aligned with the windows 26 and are not visible therethrough. Based on the user's selection of answers 7B, 10B, and 13A-13D to the diagnostic questions 6-13 that are visible through the windows 26 of the second overlay 21, and according to the criteria set forth in the diagnostic fields 27 of the second overlay 21, the user can be easily and reliably diagnosed with (or without) tension-type headaches. In the hypothetical example, the diagnosis is that there is a low probability that the user has tension-type headaches based on his/her selection of answers 6A-13D.

It is important to note that the relative spatial arrangement of the answers 6A-13D on the questionnaire form 3 and the windows 26 on the first and second overlays 20, 21 is critical to proper diagnosis. Moreover, it is important that the questionnaire form 3 be fully and properly inserted into the diagnostic file 2 so as to avoid an inaccurate diagnosis.

The headache diagnostic system 100 can be used by for self diagnosis by a user or can be used by a healthcare professional to assist in diagnosis of migraines and tension-type headaches. For example, the headache diagnostic system 100 (or just the questionnaire form 3) can be handed out to patients in the waiting room of a hospital or other healthcare facility for completion by the user. Using the diagnostic file 2, the doctor or other healthcare professional can then perform the migraine diagnosis based on the answers selected by the user on the questionnaire form 3. In other circumstances, the user can utilize the headache diagnostic system 100 to perform a self diagnosis in the convenience of his/her home or at any other location. Depending on the resulting self-diagnosis, the user can then set up an appointment with a healthcare professional for further consultation.

In some embodiments of the invention, the questionnaire form 3 can have the diagnostic questions 6-13 on both sides 14, 15. As a result, when the questionnaire form 3 is inserted into the diagnostic file 2, the user and/or healthcare professional can perform the migraine and tension-type diagnosis without having to flip the orientation of the questionnaire form 3 in the diagnostic file 2. In other embodiments of the invention, a folder-like diagnostic file does no have to be used. Instead a single overlay can be used wherein the questionnaire form is simply positioned underneath the overlay in a proper alignment.

Figure 8:
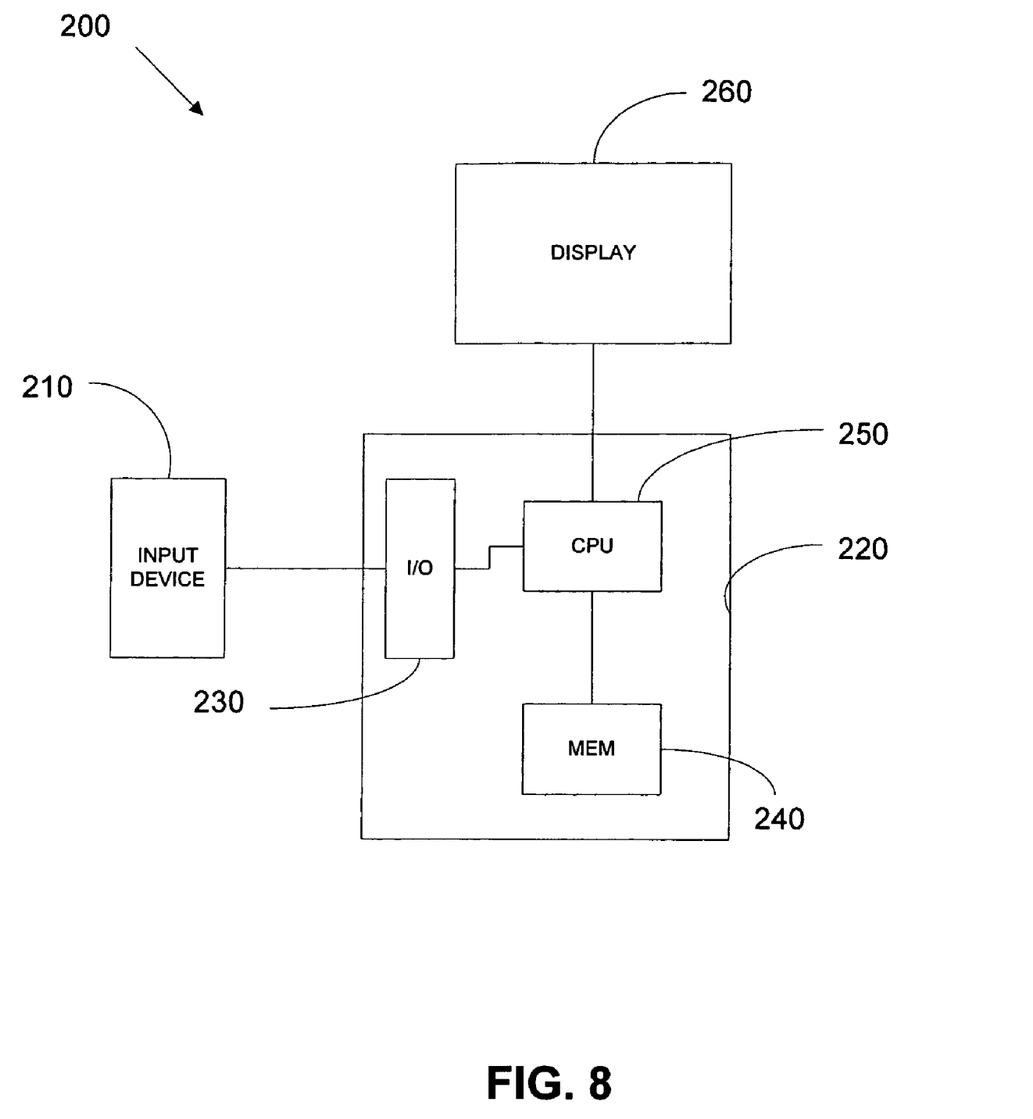
FIG. 8 is a schematic of a computer-based headache diagnostic system according to a second embodiment of the present invention.

Turning now to FIG. 8, a schematic of a computer based migraine/tension-type headache diagnostic system 200 is illustrated according to a second embodiment of the present invention. The computer-based diagnostic system 200 comprises a display module 260, a user input device 210, a signal input port 230, a suitably programmed microprocessor 250, and a computer memory medium 240. The CPU 250, the memory medium 240, and the input port 230 are located in a computer housing 220.

The CPU 250 is a suitable microprocessor based programmable logic controller, personal computer, or the like. The CPU 250 is electrically and operably coupled to all components of the system 200 that need to be controlled and/or communicated with. The display module 260 can be a computer monitor or the like. The input device 210 can be a keyboard, a mouse, a joystick, an interactive screen, or the like.

The memory medium 240 comprises sufficient memory to store all of the necessary computer code, algorithms, and data necessary for the functioning of the system 200. The CPU 250 is programmed with the proper algorithms to display an electronic version of the questionnaire form described above on the display module 260, the ability to facilitate the user to select answers on the electronic questionnaire form using the input device 210, the ability to identify the answers selected on the electronic questionnaire form that at are indicative of the user having the targeted medical condition, the ability to analyze the answers selected by the user on the electronic questionnaire form, and the ability to output a diagnosis based on the users selected answers and the analysis. As with the system 100, the computer based system 200 can be used to diagnose any medical condition(s). The diagnosis output can be simple graphical representation of a YES or NO on the display module, or can be a more-detailed diagnosis, including additional instruction on follow-up procedure and the need for definitive diagnosis If desired, the CPU 250 and the memory medium 240 can be programmed to have an electronic version of the diagnostic file and/or single overlays, and perform a virtual insertion of the diagnostic form into the diagnostic file, similar to that described above. The CPU 250 can then perform the analysis based on the location of the answers selected by the user in view of their relationship with the virtual windows. Additionally, the interface on which the electronic questionnaire form is displayed may further comprise a button that can be selected by the user to indicate that the user has completed his/her answering of the form.

The foregoing discussion discloses and describes merely exemplary embodiments of the present invention. As will be understood by those skilled in this art, the invention may be embodied in other specific forms without departing from the spirit or essential characteristics thereof.

What is claimed is:

1. A diagnostic system comprising:
    a form comprising one or more diagnostic questions and one or more possible answers to each diagnostic question;
    a first overlay comprising one or more windows and one or more diagnostic fields, wherein when the first overlay is positioned over the form, the answers to the diagnostic questions that are indicative of the user having a first medical condition are visible through the windows of the first overlay;
    wherein the one or more diagnostic fields contain criteria for diagnosing the user with the first medical condition based on the user's selection of answers on the form that are visible through the windows of the first overlay; and
    a second overlay having one or more windows and one or more diagnostic fields, wherein when the second overlay is positioned over the form, the answers indicative of the user having a second medical condition are visible through the windows of the second overlay;
    wherein the diagnostic fields of the second overlay contain criteria for diagnosing the user with the second medical condition based on the user's selection of answers that are visible through the windows of the second overlay,
    wherein the first overlay and the second overlay are connected along at least one side to form a file,
    wherein the form contains first and second sides, the form containing diagnostic questions and answer fields on both the first and second sides of the form; and
    wherein when the form is inserted into the file, the answers on the first side of the form that are indicative of the user having the first medical condition are visible through the windows of the first overlay, and the answers on the second side of the form that are indicative of the user having the second medical condition are visible through the windows of the second overlay.

2. The diagnostic system of claim 1 further:
    wherein the form comprises a plurality of diagnostic questions and corresponding answer fields;
    wherein the first overlay comprises a plurality of windows; and
    wherein answers indicative of the user having the first medical condition are visible through the windows of the first overlay when the first overlay is positioned over the form.

3. The diagnostic system of claim 2 wherein the diagnostic questions pertain to frequency of headaches, length of headaches, onset of aura symptoms, location of pain, type of pain, severity of pain, physical activities that increase or decrease headaches, or presence of additional headache-related symptoms, or any combination thereof.

4. The diagnostic system of claim 3 wherein the windows on the first overlay are arranged so that when the first overlay is positioned over the form, the answers to the diagnostic questions that are indicative of the user having a migraine are visible through the windows.

5. The diagnostic system of claim 3 wherein the windows on the first overlay are arranged so that when the first overlay is positioned over the form, the answers to the diagnostic questions that are indicative of the user having a tension-type headache are visible through the windows.

6. The diagnostic system of claim 1 wherein the first medical condition is a headache based condition.

7. The diagnostic system of claim 1 wherein the first medical condition is a tension-type headache or a migraine.

8. The diagnostic system of claim 1 wherein the first medical condition is a migraine headache and the second medical condition is a tension-type headache.

9. The diagnostic system of claim 1 wherein the answers to the diagnostic questions are arranged on the form so that when the form is positioned in the file between the first and second overlays and facing the first overlay, the answers indicative of the user having the first medical condition are visible through the windows of the first overlay.

10. The diagnostic system of claim 9 wherein the answer fields of the form are arranged so that when the form is positioned in the file between the first and second overlays and facing the second overlay, the answers indicative of the user having the second medical condition are visible through the windows of the second overlay.

11. The diagnostic system of claim 1 wherein the first overly and the second overlay are connected along two adjacent sides.

12. The diagnostic system of claim 11 wherein the first and second overlays are formed from a single piece of material that is folded in half and connected along a bottom edge.

13. The diagnostic system of claim 1 wherein the form further comprises screening questions and instructions for determining whether the user needs to answer the diagnostic questions based on the user's answers to the screening questions.

14. The diagnostic system of claim 1 wherein the first overlay is constructed of a flexible plastic, the windows being substantially transparent.

15. The diagnostic system of claim 1 wherein the windows of the first overlay are cutouts.

16. A diagnostic method comprising:
    a) answering one or more diagnostic questions pertaining to a user's health by selecting one or more answers, the one or more diagnostic questions and answers being provided on a form;
    b) positioning a first overlay having one or more windows and one or more diagnostic fields atop the form so that the answers indicative of the user having a first medical condition are visible through the windows of the first overlay;
    c) based on criteria in the diagnostic fields of the first overlay, diagnosing the user with the first medical condition based on the user's selection of answers that are visible through the windows of the first overlay;
    d) removing the first overlay from atop the form;
    e) positioning a second overlay having one or more of the windows and one or more diagnostic fields atop the form so that answers indicative of the user having a second medical condition is visible through the windows of the second overlay; and
    f) based on criteria in the diagnostic fields of the second overlay, diagnosing the user with the second medical condition based on the user's selection of answers that are visible through the windows of the second overlay, wherein the form contains first and second sides, the form containing diagnostic questions and answers on both the first and second sides of the form;

wherein the first overlay is connected to a second overlay having one or more of the windows and one or more diagnostic fields, the first and second overlays forming a file;

wherein step b) comprises inserting the form into the file so that the first side of the form faces the first overlay while the second side of the form faces the second overlay; and wherein step c) further comprises based on criteria in the diagnostic fields of the second overlay, diagnosing the user with a second medical condition based on the user's selection of answers that are visible through the windows of the second overlay.

17. The diagnostic method of claim 16 wherein step c) is a self-diagnosis performed by the user.

18. The diagnostic method of claim 16 wherein the first medical condition is a headache based condition.

19. The diagnostic method of claim 16 wherein the first medical condition is a migraine or a tension-type headache.

20. The diagnostic method of claim 16 wherein the diagnostic questions pertain to frequency of headaches, length of headaches, onset of aura symptoms, location of pain, type of pain, severity of pain, physical activities that increase or decrease headaches, or presence of additional headache-related symptoms, or any combination thereof.

21. The diagnostic method of claim 20 wherein the performance of step b) results in the answers to the diagnostic questions that are indicative of the user having a migraine being visible through the windows of the first overlay.

22. The diagnostic method of claim 20 wherein the performance of step b) results in the answers to the diagnostic questions that are indicative of the user having a tension-type headache being visible through the windows of the first overlay.

23. The diagnostic method of claim 16 wherein step e) comprises inserting the form into the file so that a side of the form having the diagnostic questions and answers is facing the second overlay.

24. The diagnostic method of claim 16 wherein the first overlay and the second overlay are connected along two adjacent sides.

25. The diagnostic system of claim 16 wherein the form contains first and second sides, the first side of the form containing screening questions and instructions for determining whether the user needs to address questions on the second side of the form, the second side of the form comprising the diagnostic questions and answers.

* * * * *